(12) United States Patent
Hocken et al.

(10) Patent No.: US 9,238,141 B2
(45) Date of Patent: Jan. 19, 2016

(54) DEVICES AND METHODS TO PROVIDE STIMULATION THERAPY IN THE PRESENCE OF EXTERNAL CONDITIONS THAT INDUCE UNDESIRABLE PERTURBATIONS

(71) Applicant: Medtronic, Inc., Minneapolis, MN (US)

(72) Inventors: Robert Hocken, Scottsdale, AZ (US); Heather Orser, Farmington, MN (US); Wesley Santa, Andover, MN (US); Larry E. Tyler, Mesa, AZ (US)

(73) Assignee: MEDTRONIC, INC., Minneapolis, MN (US)

( * ) Notice: Subject to any disclaimer, the term of this patent is extended or adjusted under 35 U.S.C. 154(b) by 13 days.

(21) Appl. No.: 13/967,638

(22) Filed: Aug. 15, 2013

(65) Prior Publication Data

US 2015/0051670 A1 Feb. 19, 2015

(51) Int. Cl.
*A61N 1/08* (2006.01)
*A61N 1/37* (2006.01)
*A61N 1/36* (2006.01)

(52) U.S. Cl.
CPC .......... *A61N 1/3718* (2013.01); *A61N 1/36125* (2013.01)

(58) Field of Classification Search
CPC .............. A61N 1/08; A61N 2001/086; A61N 1/36128; A61N 1/36142; A61N 1/36157; A61N 1/3718
USPC ................................................... 607/62, 63
See application file for complete search history.

(56) References Cited

U.S. PATENT DOCUMENTS

| | | | |
|---|---|---|---|
| 7,865,247 B2 | 1/2011 | Smith, Jr. | |
| 2007/0135868 A1* | 6/2007 | Shi et al. | 607/62 |
| 2008/0058913 A1 | 3/2008 | Gray et al. | |
| 2011/0160803 A1 | 6/2011 | Stessman et al. | |
| 2011/0276101 A1 | 11/2011 | Lee et al. | |
| 2011/0276103 A1* | 11/2011 | Maile et al. | 607/9 |
| 2013/0325085 A1* | 12/2013 | Carbunaru et al. | 607/62 |

FOREIGN PATENT DOCUMENTS

| | | |
|---|---|---|
| CN | 1138974 | 1/1997 |
| EP | 2195085 | 11/2011 |
| WO | 2007047966 | 4/2007 |
| WO | 2010111245 | 9/2010 |

OTHER PUBLICATIONS

Dinsmoor et al. "Neurostimulation Design from an Energy and Information Transfer Perspective", Bio-Medical CMOS ICs, Chapter 13, pp. 453-480, 2011.

* cited by examiner

*Primary Examiner* — Allen Porter, Jr.
(74) *Attorney, Agent, or Firm* — Withers & Keys, LLC

(57) ABSTRACT

Devices and methods compensate for perturbations in a stimulation signal caused by external conditions such as a magnetic field of an MRI machine so that stimulation therapy may continue in the presence of the external condition. Compensation for the perturbations during a stimulation pulse of a stimulation phase may be provided by using feedback within a stimulation current source. Perturbations during a recharge phase may be addressed by utilizing an active recharge at least when the external condition is present. Furthermore, compensation for perturbations during a recharge pulse of the active recharge phase may be provided by using feedback within a recharge current source. Passive recharge may be used instead of active recharge when the external condition is not present to preserve battery life of the stimulation device. The stimulation device may include a sensor to detect the external condition so that an appropriate mode of recharge may be chosen.

13 Claims, 6 Drawing Sheets

DEVICES AND METHODS TO PROVIDE STIMULATION THERAPY IN THE PRESENCE OF EXTERNAL CONDITIONS THAT INDUCE UNDESIRABLE PERTURBATIONS

TECHNICAL FIELD

Embodiments relate to electrical stimulation therapy that is provided to the body of a patient. More particularly, embodiments relate to devices and methods that provide such stimulation in the presence of external conditions that introduce perturbations into the stimulation signals.

BACKGROUND

Electrical stimulation therapy may be used for various forms of treatment. For example, stimulation therapy may be provided to address neurological issues such as chronic pain, tremors, and the like. In such an example, an implantable stimulation device is typically located in one location of convenience and is connected to electrical leads that are routed to a stimulation site such as within the brain, the spinal column, within the pelvic region, or elsewhere. The electrical leads include electrodes that interface with the tissue at the stimulation site to deliver the stimulation signals from the stimulation device.

The electrical leads include electrical conductors that span the distance from the stimulation device to the electrodes at the stimulation site, and these electrical conductors are susceptible to receiving undesired currents from induced voltages within the body caused by external conditions because of the conductive loop created from the electrodes back to the conductive case of the stimulation device when configured for unipolar stimulation. High power level deposition may then occur at the electrodes. One particular example of this situation arises when the patient undergoes a magnetic resonance image (MRI) scan. The MRI scan requires that a strong gradient magnetic field be presented to the body. Under conditions normally present when the stimulation device is actively providing unipolar stimulation signals, this magnetic field produced by the MRI machine induces voltage within the body that results in problematic currents on the leads.

The solution has been to deactivate the stimulation therapy during the MRI scan or require the stimulation to be bipolar only and to thereby present high impedances in the case to electrode path. The high impedance effectively attenuates the induced voltage and resulting current in the loop created by the leads to insignificant levels. However, the patient cannot receive unipolar stimulation therapy during this time, and this may be an unacceptable consequence, especially for life sustaining therapies.

SUMMARY

Embodiments address issues such as these and others by providing devices and methods that compensate for the perturbations caused by the external conditions in one or more of the various phases of stimulation therapy. As one example, a current source that provides the stimulation current may utilize a feedback voltage of the stimulation path that is proportional to the stimulation current to control the generation of the stimulation current and thereby compensate for the perturbations. As another example, recharge of coupling capacitors within the stimulation path may be done actively by passing current through the coupling capacitors in the direction opposite of the stimulation current to avoid creating a low impedance path during recharge. Furthermore, switches used for passive recharge may be included but held in an open state to allow the active recharge to occur when the external condition is present but may be closed to provide passive recharge when the external condition is not present to conserve battery life of the device.

Embodiments provide a method of providing stimulation to a body that involves setting a first reference voltage and generating a stimulation current in a first direction through a first output transistor, a coupling capacitor, and a first electrode during a stimulation phase. The method further involves utilizing a difference between the first reference voltage and a voltage proportional to the stimulation current to control the stimulation current through the first output transistor during the stimulation phase. The method also involves generating a recharge current in a second direction through a second output transistor, the recharge current passing through the coupling capacitor and the first electrode in a direction opposite the first direction during a recharge phase occurring at a time other than during the stimulation phase.

Embodiments provide a method of providing stimulation to a body that involves setting a first reference voltage and generating a stimulation current in a first direction through a first output transistor, a coupling capacitor, and a first electrode during a stimulation phase. The method further involves receiving exposure to a magnetic field of an MRI machine causing perturbations in the stimulation current and utilizing a difference between the first reference voltage and a voltage proportional to the stimulation current to control the stimulation current through the first output transistor during the stimulation phase to compensate for the perturbations caused by the external condition.

Embodiments provide a method of providing stimulation to a body that involves detecting a need to provide active recharge between stimulation pulses to compensate for external conditions. The method further involves responding to having detected the need to provide active recharge by opening a passive recharge switch that is in parallel with an output transistor and that connects a stimulation path including a coupling capacitor and a first electrode to a system ground when closed. The method also involves responding to having detected the need to provide active recharge by generating a recharge current through the output transistor, the recharge current passing through the coupling capacitor and the first electrode during a recharge phase in a direction opposite of stimulation current of the stimulation pulses.

Embodiments provide a device for providing stimulation therapy that includes a first current source that generates stimulation current during a stimulation phase. The first current source utilizes a difference between a first reference voltage and a feedback voltage that is proportional to the stimulation current to control the generation of the stimulation current. The stimulation current flows in a first direction through a stimulation path including a coupling capacitor and an electrode. The device includes a second current source that provides recharge current during a recharge phase, and the recharge current flows in a direction opposite the first direction through the coupling capacitor and electrode.

Embodiments provide a device for providing stimulation therapy that includes a first current source that generates stimulation current during a stimulation phase that flows in a first direction through a stimulation path that includes a coupling capacitor and an electrode. The device includes a second current source that generates recharge current during a recharge phase, and the recharge current flows in a direction opposite the first direction through the coupling capacitor and the electrode. The device includes a source switch connecting the second current source to a first power source and a recharge switch that connects the stimulation path to a common mode voltage. The device also includes a controller in communication the source switch and the recharge switch, and the controller detects whether the external condition is present. The controller communicates with the recharge switch to maintain the recharge switch in an open state when the external condition is detected and to put the recharge switch in a closed state during a recharge phase when the external condition is not detected. The controller communicates with the source switch to maintain the source switch in an open state when the external condition is not detected and to operate the source switch to activate the second current source during the recharge phase when the external condition is detected.

DETAILED DESCRIPTION

Embodiments provide devices and methods that address external conditions that may induce unwanted currents and thereby create undesirable effects within a stimulation signal. Embodiments of the device may include a stimulation engine that uses current sources having feedback to allow for control of the current to compensate for the undesirable effects caused by external conditions such as gradient magnetic fields of an MRI scan. Embodiments of the device may include current sources that are used for stimulation as well as current sources that are used for actively recharging of coupling capacitors in the stimulation path. Embodiments of the device that include current sources for actively recharging of coupling capacitors may also include switches for passively recharging the coupling capacitors and may employ active recharging in the presence of the external condition and otherwise employ passive recharging.

Figure 1:
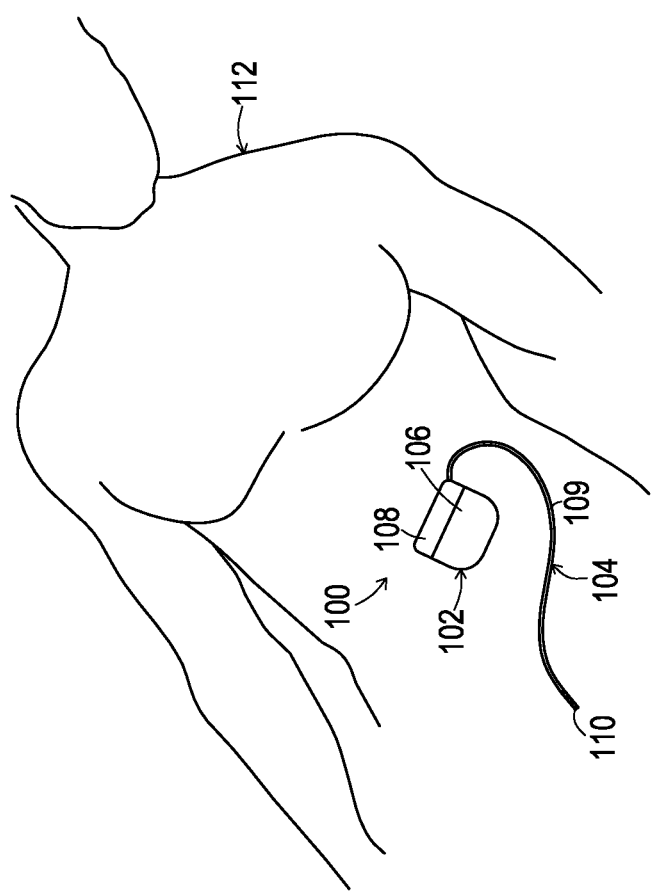
FIG. 1 shows a patient having an example of an implantable medical system according to various embodiments.

FIG. 1 shows an example of an operating environment for the various embodiments. An implantable medical system 100 is implanted within a body of a patient 112. The implantable medical system 100 includes a stimulation device 102 coupled to a stimulation lead 104. The stimulation device 102 includes a conductive outer casing 106 as well as a header 108 that includes a bore where a proximal end of the stimulation lead 104 is positioned. The stimulation lead 104 includes one or more electrodes 110 on a distal end which is positioned at a stimulation site within the body of the patient 112. The stimulation device 102 produces stimulation signals that are delivered through conductors of the stimulation lead 104 to the electrodes 110 where those stimulation signals enter the tissue of the patient 112.

Figure 2:
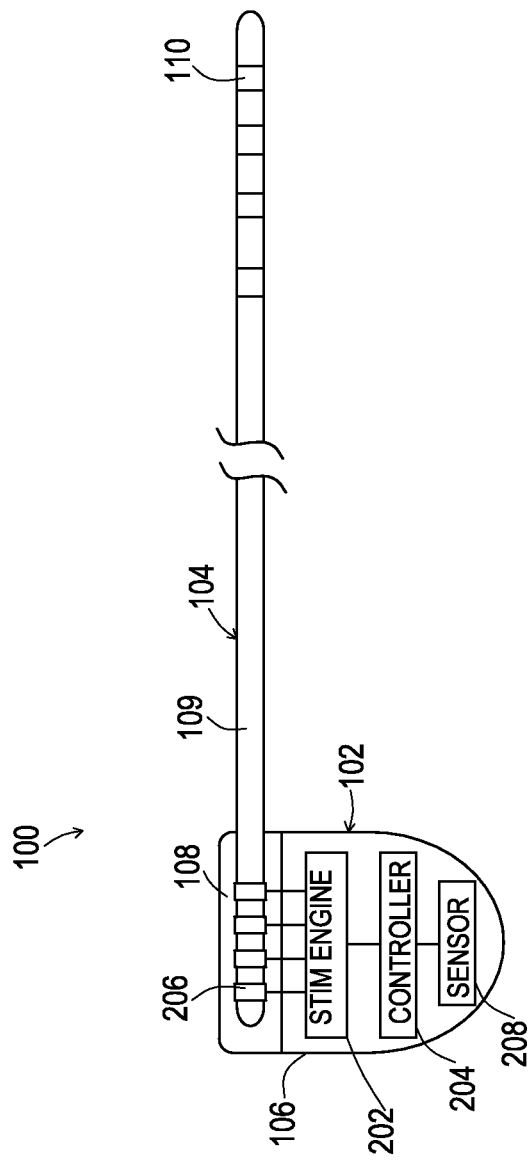
FIG. 2 shows an implantable medical system including a stimulation device and a stimulation lead.

FIG. 2 shows the implantable medical system in more detail. Here, the stimulation device 102 includes a stimulation engine 202 and a controller 204. The stimulation engine 202 produces the stimulation pulses and recharge pulses applied to the stimulation pathway via the electrical connections 206 to the lead within the header block 108. An example of a stimulation engine 202 and current sources within the stimulation engine 202 are discussed in more detail below with reference to FIGS. 4-6.

The controller 204 orchestrates the operation of the stimulation engine 202 by activating and deactivating various phases of operation of the stimulation that occur during stimulation therapy. The phases may include a precharge phase, a stimulation output phase, and a recharge phase where the recharge phase may be an active recharge output phase or passive recharge phase depending upon the circumstances. The pre-charge phase may be utilized to create a reference voltage that is used in a subsequent stimulation or active recharge output phase in conjunction with a feedback voltage from the stimulation path. A stimulation phase provides a stimulation pulse while a recharge phase clears voltage on coupling capacitors as discussed in more detail below. According to some embodiments, the controller 204 may select a passive recharge or an active recharge, where the active recharge provides a recharge pulse with the opposite polarity of the stimulation pulse.

The controller 204 may be of various forms. For instance, the controller 204 may comprise a general purpose programmable processor that implements programming instructions to bring about the operation by the stimulation engine 202 of the various phases. As other examples, the controller 204 may comprise a dedicated purpose processor and/or hardwired digital logic.

Some embodiments also include a sensor 208 that is in communication with the controller 204. The sensor 208 is used to sense the presence of an external condition. For example, the sensor 208 may be a B-field detector that can sense the magnetic field of an MRI machine. The controller 204 may configure the stimulation engine 202 depending upon whether the external condition is present. For example, when the external condition is present, the controller 204 may configure the stimulation engine 202 to employ an active recharge phase to avoid the low impedance path created by passive recharge and thereby prevent a large loop current from being induced by the external condition. The controller 204 may further configure the stimulation engine 202 to employ a passive recharge phase when the external condition is not present in order to conserve on-board battery energy.

Figure 3:
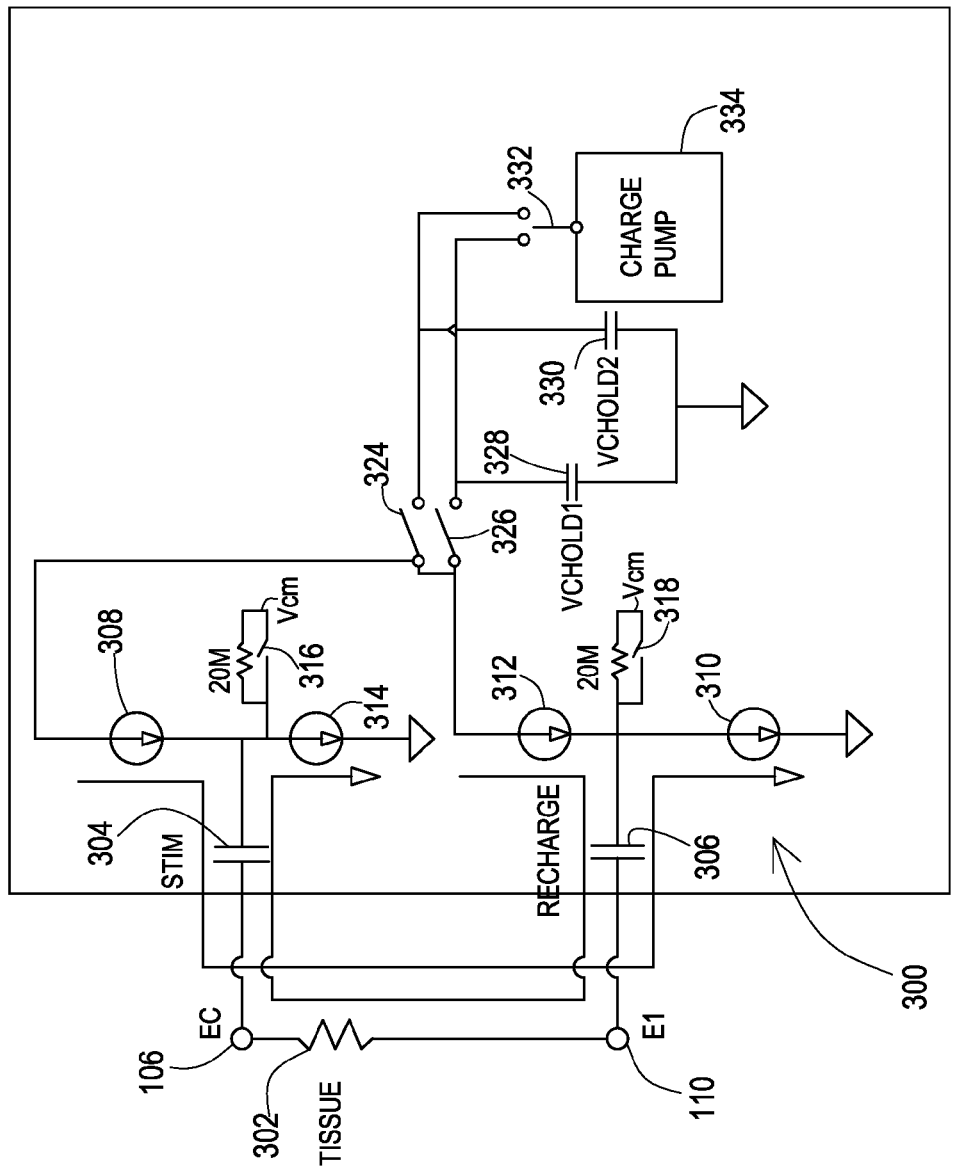
FIG. 3 shows an example of one stimulation channel of a stimulation engine of the stimulation device.

An example of a channel of the stimulation engine 202 is shown in FIG. 3. This stimulation engine 300 of FIG. 3 is connected to an "E1" electrode 110 and another electrode such as the "EC" case 106. The tissue 302 within the stimulation path between the electrode 110 and case 106 is shown as a resistor for purposes of illustration of the circuit. The stimulation pathway includes AC coupling capacitors 304, 306 that interconnect the stimulation current sources 308, 310 to the respective electrodes 110, 106.

In this example, power for the stimulation pulse is generated by a charge pump 334 that provides charge at a given voltage to one or more holding capacitors 328, 330. For embodiments that employ active recharge, either during all recharge phases or during those recharge phases when a relevant external condition is detected, one holding capacitor 328 may be used for a stimulation pulse while the other holding capacitor 330 may be used for an active recharge pulse that clears voltage from the coupling capacitors 304, 306 that builds during the stimulation pulse. A switch 332 may be used to interconnect the charge pump 334 to the particular holding capacitor 328, 330 to be charged at any given time. Furthermore, the charge pump 334 may provide a different voltage to one holding capacitor 328 relative to the other holding capacitor 330 so that the stimulation pulse and the recharge pulse are not necessarily identical in magnitude and duration, where switch 324 closes with switch 326 open to deliver energy for one pulse and switch 326 closes with switch 324 open to delivery energy for the other pulse.

The stimulation pulse is provided by activation of a pair of current sources 308, 310 which provides current in a first direction through the stimulation path including the AC coupling capacitors 304, 306, the electrodes 106, 110, and the tissue 302. For embodiments where active recharge pulses are provided either during all recharge phases or during recharge phases when an external condition is present, a pair of current sources 312, 314 provides current in a second direction through the stimulation path that is opposite the first direction subsequent to the stimulation pulse. The controller 204 activates and deactivates the current source pairings for stimulation and active recharge to achieve the stimulation current and the recharge current as shown.

For embodiments where active recharge is only provided during a recharge phase when a relevant external condition is detected and passive recharge is provided at all other recharge phases, passive recharge switches 316, 318 are included in parallel with the current sources. When the controller 204 does not detect the presence of the external condition, then rather than activate the current sources 312, 314 to provide active recharge current through the stimulation path, the controller 204 closes the switches 316, 318 to connect the coupling capacitors 304, 306 to a common mode voltage Vcm such as the system ground to thereby clear the voltage from the coupling capacitors 304, 306 during the recharge phase at a time between stimulation pulses. For embodiments where both active recharge current sources 312, 314 and passive recharge switches 316, 318 are included, the controller 204 maintains the passive recharge switches 316, 318 in an open state at all times while the external condition is present to thereby avoid creating a low impedance loop through the stimulation path.

While the use of active recharge within the stimulation engine 202 avoids creating a low impedance path, the stimulation engine 202 remains susceptible to the external condition causing unwanted perturbations in the stimulation current and the active recharge current. Eliminating such perturbations in the stimulation current and/or the active recharge current is also beneficial. Utilizing feedback within the current sources 308, 310 and/or 312, 314 allows compensation for such perturbations.

Figure 4:
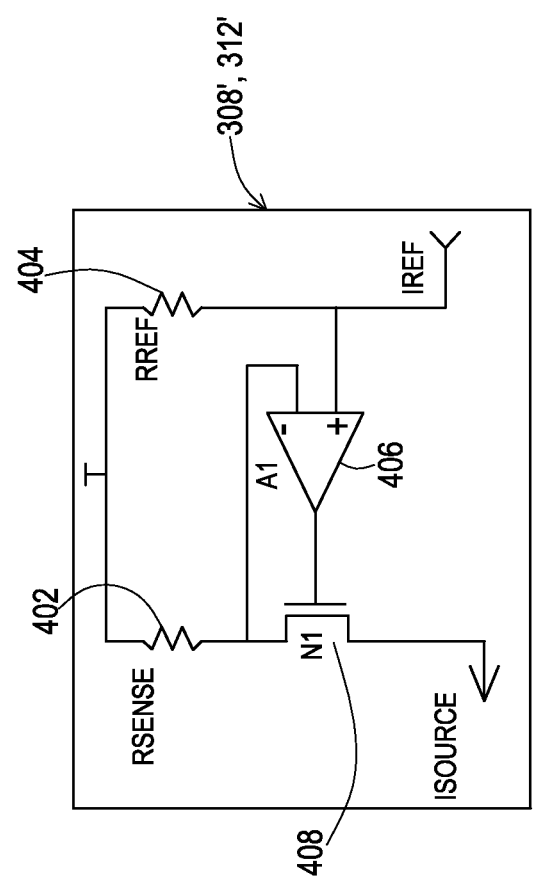
FIG. 4 shows a first example of a current source of the stimulation engine that may be used to provide stimulation current or recharge current and that utilizes feedback to control the generation of the current.

FIG. 4 shows an example 308' of the current source 308 from FIG. 3 where feedback is being employed. A reference voltage is set by passing a reference current IREF from a reference current source through a reference resistor RREF 404. This voltage is provided to an input of the amplifier 406. Likewise, the current source 308 provides a resistor RSENSE 402 in series within the stimulation path, where the ISOURCE stimulation current develops a feedback voltage across the resistor RSENSE 402 that is proportional to the ISOURCE stimulation current. This feedback voltage is provided to another input of the amplifier 406.

The resistor RREF 404 and the reference current IREF may be chosen so that the voltage across the RREF resistor 404 matches the voltage across the resistor RSENSE 402 when no perturbations from the external condition are present in the ISOURCE stimulation current. The amplifier 406 drives the gate node of an output transistor 408 that passes the ISOURCE stimulation current being generated by a power source such as one of the hold capacitors until the feedback voltage reaches the reference voltage across the RREF resistor 404 to create an active current mirror. When a perturbation is present that affects the ISOURCE current, the difference in the reference voltage and the feedback voltage causes the amplifier 406 to change the signal value being applied to the gate node of the output transistor 408, thereby affecting the operation of the output transistor 408 so as to compensate for the perturbation and restore the intended ISOURCE current.

Figure 5:
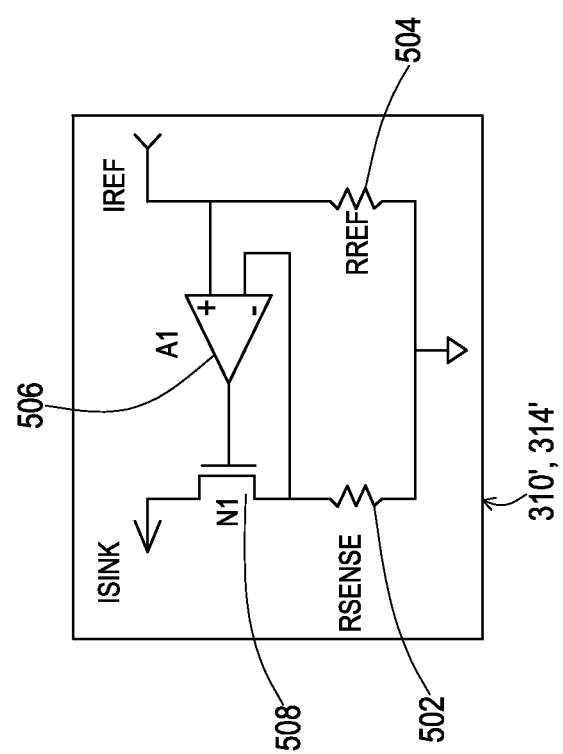
FIG. 5 shows a second example of a current source of the stimulation engine that may be used to provide stimulation current or recharge current and that utilizes feedback to control the generation of the current.

FIG. 5 shows an example 310' of the complementary current source 310 used in providing stimulation current through the stimulation path. A reference voltage is set by passing a reference current IREF through a reference resistor RREF 504. This voltage is provided to an input of the amplifier 506. Likewise, the current source 310 provides a resistor RSENSE 502 in series within the stimulation path, where the ISINK stimulation current develops a feedback voltage across the resistor RSENSE 502 that is proportional to the ISINK stimulation current. This feedback voltage is provided to another input of the amplifier 506.

The resistor RREF 504 and the reference current IREF may be chosen so that the voltage across the RREF resistor 504 matches the voltage across the resistor RSENSE 502 when no perturbations from the external condition are present in the ISINK stimulation current. The amplifier 506 drives a gate node of an output transistor 508 that passes the ISINK stimulation current until the feedback voltage reaches the reference voltage across the RREF resistor 504 to create an active current mirror. When a perturbation is present that affects the ISINK current, the difference between the reference voltage and the feedback voltage causes the amplifier 506 to change the signal value being applied to the gate node of the output transistor 508, thereby affecting the operation of the output transistor 508 so as to compensate for the perturbation and restore the intended ISINK current.

For embodiments utilizing active recharge current sources 312, 314, those current sources 312, 314 may be constructed and may operate as the current sources 312', 314' shown in FIGS. 4 and 5. The active recharge current sources 312', 314' employ reference voltages and feedback in the same manner as the current sources 308', 310' discussed above to compensate for perturbations in the recharge current from the external condition. As shown in FIG. 4, the recharge current source 312' may be configured in the same manner as the stimulation current source 308'. As shown in FIG. 5 the current source 314' may be configured in the same manner as the stimulation current source 310'.

Figure 6:
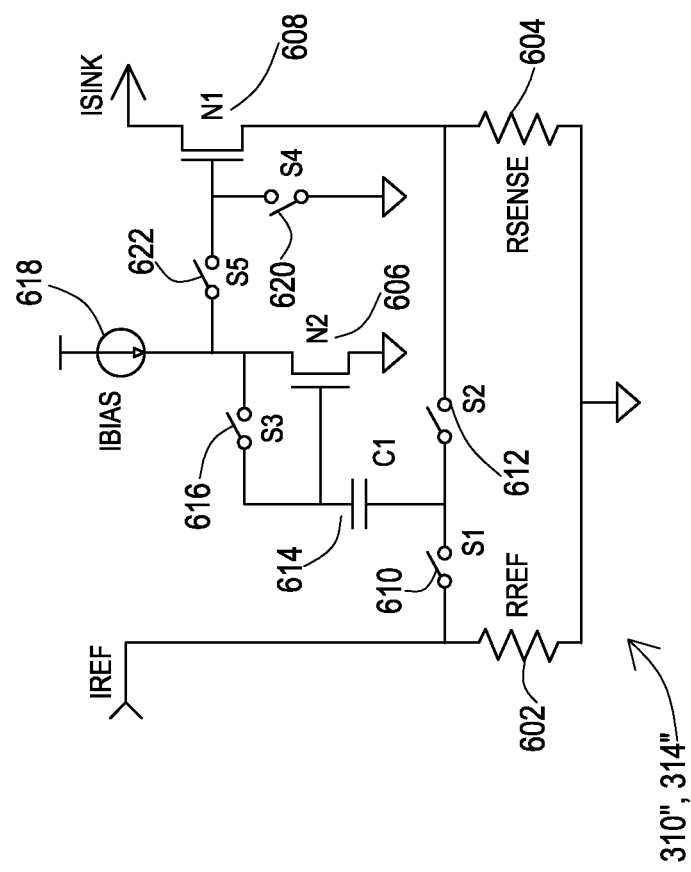
FIG. 6 shows a third example of a current source of the stimulation engine that may be used to provide stimulation current or recharge current where a voltage that is used in conjunction with the feedback is stored within a capacitor prior to providing stimulation or recharge current.

Another example 310" of the stimulation current source 310 of FIG. 3 that utilizes a feedback voltage to compensate for perturbations in the stimulation current caused by the external condition is shown in FIG. 6. The recharge current source 314 may be configured in the same manner as demonstrated by recharge current source 314" in FIG. 6. In this example, the stimulation phase and/or recharge phase includes a precharge phase that precedes the production of the stimulation pulse or recharge pulse. During the precharge phase, a switch 610, a switch 616, and a switch 620 are closed while other switches are open and a reference current IREF passes through a reference resistor RREF 602. The voltage across the reference resistor RREF 602 is applied to one terminal of a reference capacitor 614. A current source 618 provides a bias current IBIAS to a reference transistor 606, and the opposite terminal of the reference capacitor 614 acquires the voltage potential of a gate node of the reference transistor 606. Thus, the capacitor 614 stores a voltage that is equal to the difference between the voltage on the gate node of the reference transistor 606 and the voltage across the reference resistor RREF 602.

After the precharge phase, the stimulation current or recharge current is provided during an output phase. A switch 612 and a switch 622 are closed while all other switches are open. A resistor RSENSE 604 is in series within the stimulation path, where the ISINK stimulation current flows and develops a feedback voltage across the resistor RSENSE 604 that is proportional to the ISINK current. This feedback voltage is applied to the terminal of the reference capacitor 614 that previously received the voltage across the resistor RREF 602 during the prior precharge phase. Thus, the voltage potential applied to the gate of the reference transistor 606 fluctuates according to fluctuation in the feedback voltage.

The gate node of the output transistor 608 is connected to the current source 618 together with the reference transistor 606. A difference in the reference voltage applied to the gate node of the reference transistor 606 due to the feedback voltage coupled to the reference capacitor 614 differing from the reference voltage across resistor RREF 602 results in a change to the output of the current source. As an example of operation, if the voltage on resistor RSENSE 604 is lower than the precharge reference voltage across the resistor RREF 602, then the gate of the reference transistor 606 is pulled lower, allowing the IBIAS current source 618 to pull up on the gate of the output transistor 608 so that the output transistor 608 will pass more current through the resistor RSENSE 604. This feedback mechanism mirrors the voltage from the resistor RREF 602 occurring during the precharge phase to the resistor RSENSE 604 during the output phase.

The stimulation current source 308, or recharge current source 312, may be configured in the complementary manner to the circuit shown in FIG. 6, where an RSENSE resistor is present in the ISOURCE current path and the feedback to the reference capacitor is in relation to the ISOURCE current.

Accordingly, these various embodiments discussed above provide compensation to reduce induced effects within the stimulation path at any given phase of the stimulation signal due to external conditions including the magnetic field of an MRI machine. By compensating to reduce these induced effects at one or more of the phases of the stimulation signal, the likelihood of safely operating the stimulation device 102 during the MRI scan is increased. Embodiments that apply compensation by using feedback during the stimulation output phase, apply an active recharge, and apply further compensation by using feedback during the active recharge output phase provide the highest likelihood of safely operating the stimulation device 102 during the MRI scan.

While embodiments have been particularly shown and described, it will be understood by those skilled in the art that various other changes in the form and details may be made therein without departing from the spirit and scope of the invention.

What is claimed is:

1. A method of providing stimulation to a body, comprising:
  setting a first reference voltage;
  generating from a power source a stimulation current in a first direction through a first current source, a second current source, a coupling capacitor, and a first electrode during a stimulation phase to provide the stimulation to the body, the first current source comprising a first output transistor configured in a first current mirror and the second current source comprising a second output transistor configured in a second current mirror;
  utilizing by at least the first current mirror a difference between the first reference voltage and a voltage that is proportional to the stimulation current and that is obtained from a stimulation path that includes the first output transistor, the second output transistor, the coupling capacitor, and the first electrode to control the stimulation current through the first output transistor during the stimulation phase; and
  generating from the power source a recharge current in a second direction through a third output transistor, the recharge current passing through the coupling capacitor and the first electrode in a direction opposite the first direction during a recharge phase occurring at a time other than during the stimulation phase; and
  detecting an external condition that causes perturbations in the stimulation current, and wherein generating the recharge current in the second direction through the third output transistor is done in response to detecting the external condition.

2. The method of claim 1, further comprising:
  setting a second reference voltage; and
  utilizing a difference between the second reference voltage and a voltage proportional to the recharge current to control the recharge current through the third output transistor during the recharge phase.

3. The method of claim 1, further comprising closing a passive recharge switch that once closed connects a stimulation path including the first electrode and the first coupling capacitor to a system ground at a time between stimulation pulses when not detecting the external condition.

4. The method of claim 1, wherein setting the first reference voltage comprises passing a reference current through a reference resistor to produce a voltage across the reference resistor.

5. The method of claim 1, wherein utilizing the difference between the first reference voltage and the voltage proportional to the stimulation current to control the stimulation current comprises passing the stimulation current through a feedback resistor to produce the voltage proportional to the stimulation current across the feedback resistor.

6. The method of claim 5, wherein utilizing the difference between the first reference voltage and the voltage proportional to the stimulation current to control the stimulation current further comprises storing a voltage within a reference capacitor related to the first reference voltage prior to generating the stimulation current, and applying the stored voltage between a node of a reference transistor and a node of the feedback resistor having the voltage that is proportional to the stimulation current while the reference transistor passes a bias current that is mirrored through the first output transistor.

7. The method of claim 1, further comprising receiving exposure to a magnetic field of an MRI machine that causes perturbations in the stimulation current, and wherein utilizing a difference between the first reference voltage and a voltage proportional to the stimulation current to control the stimulation current through the first output transistor during the stimulation phase compensates for the perturbations caused by the magnetic field.

8. The method of claim 1, wherein detecting the external condition comprises sensing the presence of the external condition.

9. The method of claim 1, wherein the external condition comprises a magnetic field of an MRI machine.

10. A method of providing stimulation to a body, comprising:

setting a first reference voltage;
generating from a power source a stimulation current in a first direction through a first output transistor configured in a first current mirror, a coupling capacitor, and a first electrode during a stimulation phase;
utilizing by the first current mirror a difference between the first reference voltage and a voltage proportional to the stimulation current to control the stimulation current through the first output transistor during the stimulation phase to provide the stimulation to the body;
detecting an external condition that comprises a magnetic field of an MRI machine; and
in response to detecting the external condition, generating from the power source a recharge current in a second direction through a third output transistor, the recharge current passing through the coupling capacitor and the first electrode in a direction opposite the first direction during a recharge phase occurring at a time other than during the stimulation phase.

11. A method of providing stimulation to a body, comprising:
setting a first reference voltage;
generating from a power source a stimulation current in a first direction through a first current source, a second current source, a coupling capacitor, and a first electrode during a stimulation phase to provide the stimulation to the body, the first current source comprising a first output transistor configured in a first current mirror and the second current source comprising a second output transistor configured in a second current mirror;
utilizing by at least the first current mirror a difference between the first reference voltage and a voltage that is proportional to the stimulation current and that is obtained from a stimulation path that includes the first output transistor, the second output transistor, the coupling capacitor, and the first electrode to control the stimulation current through the first output transistor during the stimulation phase; and
generating from the power source a recharge current in a second direction through a third output transistor, the recharge current passing through the coupling capacitor and the first electrode in a direction opposite the first direction during a recharge phase occurring at a time other than during the stimulation phase;
setting a second reference voltage; and
utilizing a difference between the second reference voltage and a voltage proportional to the recharge current to control the recharge current through the third output transistor during the recharge phase, wherein utilizing the difference between the first reference voltage and the voltage proportional to the stimulation current and utilizing the difference between the second reference voltage and the voltage proportional to the recharge current are done in the presence of an external condition causing perturbations in the stimulation current.

12. A method of providing stimulation to a body, comprising:
setting a first reference voltage;
generating from a power source a stimulation current in a first direction through a first current source, a second current source, a coupling capacitor, and a first electrode during a stimulation phase to provide the stimulation to the body, the first current source comprising a first output transistor configured in a first current mirror and the second current source comprising a second output transistor configured in a second current mirror;
utilizing by at least the first current mirror a difference between the first reference voltage and a voltage that is proportional to the stimulation current and that is obtained from a stimulation path that includes the first output transistor, the second output transistor, the coupling capacitor, and the first electrode to control the stimulation current through the first output transistor during the stimulation phase; and
generating from the power source a recharge current in a second direction through a third output transistor, the recharge current passing through the coupling capacitor and the first electrode in a direction opposite the first direction during a recharge phase occurring at a time other than during the stimulation phase, wherein utilizing the difference between the first reference voltage and the voltage proportional to the stimulation current to control the stimulation current comprises passing the stimulation current through a feedback resistor to produce the voltage proportional to the stimulation current across the feedback resistor, and wherein utilizing the difference between the first reference voltage and the voltage proportional to the stimulation current to control the stimulation current further comprises storing a voltage within a reference capacitor related to the first reference voltage prior to generating the stimulation current, and applying the stored voltage between a node of a reference transistor and a node of the feedback resistor having the voltage that is proportional to the stimulation current while the reference transistor passes a bias current that is mirrored through the first output transistor.

13. A method of providing stimulation to a body, comprising:
setting a first reference voltage;
generating from a power source a stimulation current in a first direction through a first current source, a second current source, a coupling capacitor, and a first electrode during a stimulation phase to provide the stimulation to the body, the first current source comprising a first output transistor configured in a first current mirror and the second current source comprising a second output transistor configured in a second current mirror;
utilizing by at least the first current mirror a difference between the first reference voltage and a voltage that is proportional to the stimulation current and that is obtained from a stimulation path that includes the first output transistor, the second output transistor, the coupling capacitor, and the first electrode to control the stimulation current through the first output transistor during the stimulation phase; and
generating from the power source a recharge current in a second direction through a third output transistor, the recharge current passing through the coupling capacitor and the first electrode in a direction opposite the first direction during a recharge phase occurring at a time other than during the stimulation phase; and
receiving exposure to a magnetic field of an MRI machine that causes perturbations in the stimulation current, and wherein utilizing a difference between the first reference voltage and a voltage proportional to the stimulation current to control the stimulation current through the first output transistor during the stimulation phase compensates for the perturbations caused by the magnetic field.

* * * * *